United States Patent
Tsai et al.

(10) Patent No.: US 10,376,857 B1
(45) Date of Patent: Aug. 13, 2019

(54) APPARATUS, SYSTEMS AND METHODS FOR MICROFLUIDIC VACUUM SHRINKAGE OF MICROBUBBLES

(71) Applicants: Scott Tsai, Toronto (CA); Raffi Karshafian, Scarborough (CA); Michael Kolios, Hamilton (CA); Byeong-Ui Moon, Longueuil (CA); Vaskar Gnyawali, Toronto (CA)

(72) Inventors: Scott Tsai, Toronto (CA); Raffi Karshafian, Scarborough (CA); Michael Kolios, Hamilton (CA); Byeong-Ui Moon, Longueuil (CA); Vaskar Gnyawali, Toronto (CA)

( * ) Notice: Subject to any disclaimer, the term of this patent is extended or adjusted under 35 U.S.C. 154(b) by 2 days.

(21) Appl. No.: 15/944,453

(22) Filed: Apr. 3, 2018

(51) Int. Cl.
*G01N 35/08* (2006.01)
*B01J 19/00* (2006.01)
(Continued)

(52) U.S. Cl.
CPC ............. *B01J 10/002* (2013.01); *B01J 3/006* (2013.01); *B01J 3/062* (2013.01); *B01J 19/0006* (2013.01);
(Continued)

(58) Field of Classification Search
CPC ....... B01L 2200/0673; B01L 3/502784; B01L 2400/0415; B01L 2200/027; B01L 2200/0605; B01L 2200/0647; B01L 2200/0652; B01L 2200/0689; B01L 2200/10; B01L 2300/0816;
(Continued)

(56) References Cited

U.S. PATENT DOCUMENTS

| 5,366,347 A * | 11/1994 | Hoglund ................. F04C 19/00 415/169.1 |
| 2008/0200343 A1* | 8/2008 | Clemens ........... B01L 3/502715 506/9 |

(Continued)

OTHER PUBLICATIONS

Hettiarachchi et al. "On-chip generation of microbubbles as a practical technology for manufacturing contrast agents for ultrasonic imaging", Lab Chip, 2007, 7, 463-468.
(Continued)

*Primary Examiner* — Jennifer Wecker
(74) *Attorney, Agent, or Firm* — Bereskin & Parr LLP/S.E.N.C.R.L., s.r.l.; Tony Orsi

(57) ABSTRACT

Methods and apparatuses for controlling the size of microbubbles are provided herein. The methods include forming a microbubble in a liquid at an inlet end of a liquid microchannel, the liquid microchannel having an outlet end spaced from the inlet end and a liquid microchannel conduit extending therebetween. As the liquid is propelled along a length of the liquid microchannel, the liquid carry the microbubble, a negative pressure is applied to a first very low pressure microchannel having a first end, a second end spaced from the first end and a first very low pressure microchannel conduit extending between the first end and the second end and having a portion thereof being laterally spaced from and adjacent to a portion of the liquid microchannel conduit. The negative pressure withdraws air from the microbubble in the liquid microchannel to shrink the microbubble as the microbubble travels along the portion of the liquid microchannel conduit.

20 Claims, 4 Drawing Sheets

(51) Int. Cl.
*B01J 3/00* (2006.01)
*B01L 3/00* (2006.01)
*B01J 10/00* (2006.01)
*B01J 3/06* (2006.01)
*A61K 49/22* (2006.01)

(52) U.S. Cl.
CPC .......... *B01L 3/50273* (2013.01); *G01N 35/08* (2013.01); *A61K 49/223* (2013.01); *B01J 2219/00162* (2013.01); *B01J 2219/00164* (2013.01); *B01L 3/502715* (2013.01); *B01L 2200/0647* (2013.01); *B01L 2200/0673* (2013.01); *B01L 2200/10* (2013.01); *B01L 2400/0487* (2013.01)

(58) Field of Classification Search
CPC ..... B01L 2300/0838; B01L 2300/0867; B01L 2300/0883; B01L 2300/1805; B01L 2400/0424; B01L 2400/0487; B01L 2400/082; B01L 2400/086; B01L 3/0241; B01L 3/0265; B01L 3/502715; B01L 3/50273; B01L 3/502738; B01L 3/502746; B01L 3/502753; B01L 3/502761; B01L 7/00; G01N 35/08; G01N 15/1404; G01N 15/1434; G01N 2015/1413; G01N 2015/1422; G01N 2015/149; G01N 2035/1048; G01N 2333/942; G01N 33/573; B01F 13/0071; B01F 13/0076; B01F 2215/0037
See application file for complete search history.

(56) References Cited

U.S. PATENT DOCUMENTS

| | | |
|---|---|---|
| 2011/0114190 A1 | 5/2011 | Wen et al. |
| 2015/0174576 A1 | 6/2015 | Van Vliet et al. |
| 2016/0332131 A1 | 11/2016 | Lee et al. |
| 2017/0354973 A1 | 12/2017 | Sustarich et al. |

OTHER PUBLICATIONS

Farook et al. "Preparation of suspensions of phospholipid-coated microbubbles by coaxial electrohydrodynamic atomization", J. R. Soc. Interface (2009) 6, 271-277, doi:10.1098/rsif.2008.0225 Published online Jul. 22, 2008.
Park et al. "A microfluidic route to small CO2 microbubbles with narrow size distribution", Soft Matter, 2010, 6, 630-634.
Shih et al. "Flow-focusing regimes for accelerated production of monodisperse drug-loadable microbubbles toward clinical-scale applications", Lab Chip, 2013, 13, 4816-4826.
Radisic et al. "Microfabricated perfusable cardiac biowire: a platform that mimics native cardiac bundle", Lab Chip, 2014, 14, 869-882.
Seo et al. "Size reduction of cosolvent-infused microbubbles to form acoustically responsive monodisperse perfluorocarbon nanodroplets", Lab Chip, 2015, 15, 3581-3590.
Shih et al. "Post-Formation Shrinkage and Stabilization of Microfluidic Bubbles in Lipid Solution", Langmuir 2016, 32, 1939-1946.
Gnyawali et al. "Honey, I shrunk the bubbles: microfluidic vacuum shrinkage of lipid-stabilized microbubbles", Soft Matter, 2017,13, 4011-4016.
Salari et al. "Shrinking microbubbles with microfluidics: mathematical modelling to control microbubble sizes", Soft Matter, 2017, 13, 8796-8806.
Pham et al. "Steering air bubbles with an add-on vacuum layer for biopolymer membrane biofabrication in PDMS microfluidics", Lab Chip, 2017, 17, 248-255.
Daeyeon Lee "Recombinant Protein-Stabilized Microbubbles for Potential Applications in Cancer Theranostics" 9th Annual LRSM/UPR PREM Symposium, "Structure and Properties of Biopolymers", Sheraton Old San Juan Hotel Friday, May 6, 2016, University of Puerto Rico & The Laboratory for Research on the Structure of Matter; see: https://vimeo.com/166816640.
Moon, Byeong-Ui, Dae Kun Hwang, and Scott Sh Tsai. "Shrinking, growing, and bursting: microfluidic equilibrium control of water-in-water droplets." Lab on a Chip 16.14 (2016): 2601-2608.
Needles et al. VisualSonics White Paper: Nonlinear Contrast Agent Imaging with a High Frequency Linear Array Based System. Apr. 14, 2009, version 1.0. (https://www.visualsonics.com/sites/default/files/WP_2100_NA_Nonlinear_Contrast_Agent.pdf).
Sirsi and Borden, "Microbubble Compositions, Properties and Biomedical Applications" Bubble Sci Eng Technol. Nov. 2009; 1(1-2): 3-17.
Stride et al. "Novel preparation techniques for controlling microbubble uniformity: a comparison". Med Biol Eng Comput (2009) 47: 883-892.
Dayton et al. "Targeted Imaging Using Ultrasound", Journal of Magnetic Resonance Imaging 16: 362-377 (2002).
Karshafian et al. "Sonoporation by Ultrasound-Activated Microbubble Contrast Agents: Effect of Acoustic Exposure Parameters on Cell Membrane Permeability and Cell Viability", Ultrasound in Med. & Biol., vol. 35, pp. 847-860, 2009.
Qin et al. "Ultrasound contrast microbubbles in imaging and therapy: physical principles and engineering", Phys. Med. Biol. 54 (2009) R27-R57.
Streeter et al. "Improving Sensitivity in Ultrasound Molecular Imaging by Tailoring Contrast Agent Size Distribution: In Vivo Studies", Molecular Imaging, vol. 9, No. 2 (Mar./Apr. 2010): pp. 87-95.
Ma et al. Diagnostic and therapeutic research on ultrasound microbubble/nanobubble contrast agents (Review), Molecular Medicine Reports 12: 4022-4028, 2015.
Shohet et al. "Echocardiographic Destruction of Albumin Microbubbles Directs Gene Delivery to the Myocardium", Circulation. 2000; 101: 2554-2556.

* cited by examiner

APPARATUS, SYSTEMS AND METHODS FOR MICROFLUIDIC VACUUM SHRINKAGE OF MICROBUBBLES

FIELD

This disclosure relates generally to apparatus, systems and methods for controlling microbubble size, and more specifically to apparatus, systems and methods for shrinking microbubbles using a vacuum.

BACKGROUND

Microbubbles are used as contrast agents in a variety of clinical applications, ranging from imaging, diagnostics, to therapeutics. These microbubbles are typically injected into veins to disperse in the blood stream and circulate throughout the body.

In ultrasound imaging applications, suspended microbubbles that are insonified by ultrasound pulses oscillate when the ultrasound is at a frequency near the microbubbles' resonance frequency. This oscillation causes the rapid expansion and contraction of the bubble, producing strong ultrasound echoes. Signals from the echoes increase the image contrast of the blood stream, thereby improving the visual distinction between blood and the surrounding tissues. This improvement leads to increased resolution, detection sensitivity, and accuracy of imaging, thereby facilitating enhanced detection of thrombosis and diseased tissues.

Recently, microbubbles have started to also be utilized for therapeutics. Namely, microbubbles have been applied to gene delivery and drug delivery. Further, sonoporation operations use acoustic streaming from vibrating microbubbles to produce pores on the membrane of tumor cells to lyse the cells or selectively deliver genes and/or drugs for cancer treatment.

Despite the promise of microbubble technology in a range of different biomedical applications, it remains challenging to produce monodisperse (uniform size) microbubbles. In the aforementioned applications, the microbubbles required are typically 1 to 7 µm in diameter. Conventional methods used to generate microbubbles such as sonification, high shear emulsification, inkjet printing and coaxial electrohydrodynamic atomization (CEHDA), create polydisperse (i.e. variable size) microbubbles at diameters less than 10 µm. As a result of the microbubbles' polydispersity, subsequent filtration steps are needed to attain microbubbles in a range of 1-7 µm.

While microfluidic techniques produce monodisperse (i.e. uniform size) microbubbles with excellent size-control, microfluidics generated microbubbles have lower limits of size that directly depend on the dimensions of the bubble generating microchannel orifice. Making microbubbles that are on the relevant length scale of ultrasound and therapeutics applications requires orifice widths that are less than 10 micrometers wide. Fabricating microfluidic molds with such orifice widths is expensive and requires high-resolution photolithography.

Accordingly, there is a need for new methods, systems and apparatuses for forming microbubbles with diameters of just a few micrometers.

SUMMARY

In accordance with a broad aspect, there is provided a method of controlling a size of a microbubble. The method includes forming a microbubble in a liquid at an inlet end of a liquid microchannel, the liquid microchannel having an outlet end spaced from the inlet end and a liquid microchannel conduit extending between the inlet end and the outlet end. The method also includes propelling the liquid along a length of the liquid microchannel from the inlet end towards the outlet end, the liquid carrying the microbubble from the inlet end towards the outlet end, and applying a negative pressure to a first very low pressure microchannel, the first very low pressure microchannel having a first end, a second end spaced from the first end and a first very low pressure microchannel conduit extending between the first end and the second end and having a portion thereof being laterally spaced from and adjacent to a portion of the liquid microchannel conduit. The negative pressure withdrawing air from the microbubble in the liquid microchannel shrinks the microbubble as the microbubble travels along the portion of the liquid microchannel conduit laterally spaced from and adjacent to the portion of the first very low pressure microchannel conduit.

In at least one embodiment, the method further includes applying the negative pressure to the first very low pressure microchannel and to a second very low pressure microchannel, the second very low pressure microchannel having a first end, a second end spaced from the first end and a second very low pressure microchannel conduit extending between the first end and the second end, a portion of the second very low pressure microchannel conduit being laterally spaced from and adjacent to an opposed side of the portion of the liquid microchannel conduit relative to the portion of the first very low pressure microchannel conduit.

In at least one embodiment, the portion of the first very low pressure microchannel conduit laterally spaced from and adjacent to the portion of the liquid microchannel conduit is parallel to the portion of the liquid microchannel conduit.

In at least one embodiment, the portions of the first very low pressure microchannel conduit and the second very low pressure microchannel conduit that are laterally spaced from and adjacent to the portion of the liquid microchannel conduit are both parallel to the portion of the liquid microchannel conduit.

In at least one embodiment, after the forming of the microbubble, the microbubble has a width in a range of about 10 to 1000 µm and after the shrinking of the microbubble the microbubble has a width in a range of about 1 to 7 µm.

In at least one embodiment, the negative pressure is in a range of about 0 to 90 kPa below atmospheric pressure.

In at least one embodiment, the negative pressure is in a range of about 50 to 70 kPa below atmospheric pressure.

In at least one embodiment, the liquid is introduced into the microchannel at a flow rate in a range of about 1 to 100 µL per minute.

In at least one embodiment, the liquid is introduced into the microchannel at a flow rate of about 4 µL per minute.

In accordance with a broad aspect, an apparatus for shrinking microbubbles is provided herein. The apparatus includes a liquid microchannel having an inlet end, an outlet end spaced from the inlet end and a liquid conduit extending between the inlet end and the outlet end, the liquid microchannel housing a liquid having a microbubble dispersed in the liquid, the microbubble travelling along with the liquid in the liquid microchannel from the inlet end to the outlet end. The apparatus also includes a first very low pressure microchannel having a first end, a second end spaced from the first end and a first very low pressure microchannel conduit extending between the first end and the second end, the first end of the first very low pressure microchannel being coupled to a vacuum source for creating a negative pressure in the first very low pressure microchannel. A portion of the first very low pressure microchannel conduit is laterally spaced from and adjacent to a portion of the liquid microchannel conduit and the negative pressure withdraws air from the microbubble in the liquid microchannel conduit to shrink the microbubble as the microbubble travels along the portion of the liquid microchannel conduit laterally spaced from and adjacent to the portion of the first very low pressure microchannel conduit.

In at least one embodiment, the apparatus also includes a second very low pressure microchannel, the second very low pressure microchannel having a first end, a second end spaced from the first end and a second very low pressure microchannel conduit extending between the first end and the second end, the first end of the second very low pressure microchannel being coupled to a vacuum source for creating a negative pressure in the second very low pressure microchannel. A portion of the second very low pressure microchannel conduit is laterally spaced from and adjacent to an opposed side of the portion of the liquid microchannel conduit relative to the portion of the first very low pressure microchannel conduit.

In at least one embodiment, the portion of the first very low pressure microchannel conduit laterally spaced from and adjacent to the portion of the liquid microchannel conduit is parallel to the portion of the liquid microchannel conduit.

In at least one embodiment, the portions of the first and second very low pressure microchannel conduits laterally spaced from and adjacent to the portion of the liquid microchannel conduit are both parallel to the portion of the liquid microchannel conduit.

In at least one embodiment, a spacing between the portion of the liquid microchannel conduit and the portion of the first very low pressure microchannel conduit is about 175 μm.

In at least one embodiment, the liquid microchannel has a liquid microchannel width and the liquid microchannel width decreases along a length of the liquid microchannel between the inlet end and the outlet end.

In at least one embodiment, the first very low pressure microchannel has a first very low pressure microchannel width of about 150 μm.

In at least one embodiment, the negative pressure is in a range of about 0 to 90 kPa below atmospheric pressure.

In at least one embodiment, the negative pressure is in a range of about 50 to 70 kPa below atmospheric pressure.

In at least one embodiment, the liquid is introduced into the liquid microchannel at a flow rate of about 4 μL per minute.

In at least one embodiment, the liquid microchannel has a serpentine shape and the first very low pressure microchannel is arranged to be interdigitated within curves of the liquid microchannel.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
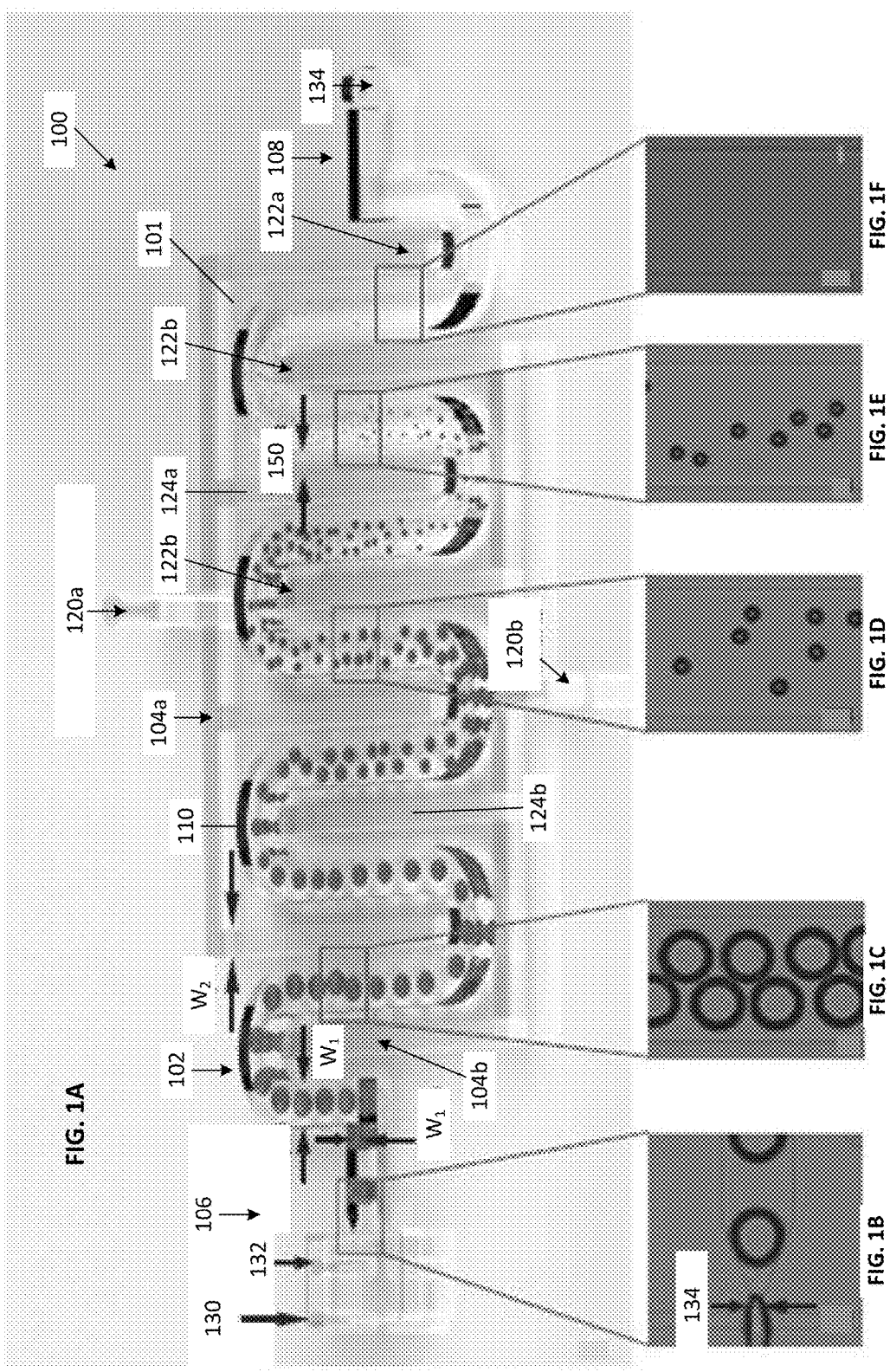
FIG. 1A is a perspective view of an example embodiment of a microfluidic device for microbubble generation and shrinkage, in accordance with the teachings herein.
FIGS. 1B-1F are top down images of microbubbles formed in the microfluidic device of FIG. 1A showing sequential shrinking of the microbubbles as they flow through a microchannel.

Further aspects and features of the example embodiments described herein will appear from the following description taken together with the accompanying drawings.

DESCRIPTION OF EXAMPLE EMBODIMENTS

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

The following description is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

In spite of the technologies that have been developed, there remains a need in the field for improvements in the development of apparatuses, systems and methods for forming microbubbles. In accordance with the teachings herein, various embodiments are described for apparatuses, systems and methods that may use a vacuum source to consistently, repeatably and accurately form microbubbles and control their size.

In accordance with one aspect, a microfluidic device that uses suction to shrink bubbles generated from a microfluidic flow-focusing orifice into microbubbles that are on the relevant length-scale for ultrasound and therapeutic applications (e.g. in a range of about 100 nm to about 7 µm, or in a range of about 1 µm to about 7 µm) is described. Herein, the terms "suction", "negative pressure" and/or "vacuum pressure" are used to refer to a pressure that is lower than atmospheric pressure, or lower than about 101.3 kPa. Accordingly, it should be noted that the term a "very low pressure" includes a "vacuum pressure" and that the term "very low pressure microchannel" can also be known as a vacuum microchannel Further, it should be noted that the term microbubble is also meant to cover nanobubbles that are generated with a size of less than 1 micrometer.

In accordance with another aspect, the microfluidic device may also be used to control shell characteristics (e.g. shell buckling) of microbubbles passing through a liquid microchannel of the device. For instance, controlling shell characteristics (e.g. shell buckling) of microbubbles within the liquid microchannel may generate microbubbles with unique non-linear acoustic characteristics. Microbubble shell characteristics (e.g. shell buckling) may be associated with shrinkage of microbubbles or may be controlled independently from microbubble shrinkage. Tissues do not scatter sound non-linearly so microbubbles with buckled shell characteristics may generate a very large contrast in ultrasound imaging.

The microfluidic device may be formed by soft lithography techniques and may have embedded very low pressure microchannels laterally spaced from and adjacent to a central liquid-filled microchannel through which the microbubbles flow. By tuning a negative pressure in the very low pressure microchannels that are laterally spaced from and adjacent to the central liquid-filled microchannel, it may be possible to controllably shrink the microbubbles in the central liquid-filled microchannel as they flow past a portion of the very low pressure microchannel that is adjacent to a laterally spaced from the central liquid-filled microchannel from an inlet end of the central liquid-filled microchannel to an outlet end. For instance, it may be possible to shrink the microbubbles to a relevant length-scale for ultrasound and therapeutics applications and to seven sub-micrometer length-scales.

Turning to the Figures, FIG. 1A is a perspective view of an example embodiment of a microfluidic device 100 for microbubble generation and microbubble shrinking, in accordance with the teachings herein.

FIG. 1A shows a microfluidic device 100 having a body 101 defining a liquid microchannel 102 and two very low pressure (e.g. vacuum) microchannels 104a, 104b for forming and controllably shrinking microbubbles. It should be understood that the microfluidic device 100 may have one very low pressure microchannel 104 or may have more than two very low pressure microchannels 104 in different embodiments. In the example shown in FIG. 1A, the two very low pressure microchannels 104a, 104b are positioned to be spaced from and adjacent to the liquid microchannel 102 along a length of the liquid microchannel 102.

Liquid microchannel 102 has a first (i.e. inlet) end 106, a second (i.e. outlet) end 108 and a conduit 110 running between the inlet and outlet ends 106, 108. Liquid microchannel 102 may be any appropriate shape in cross-section to provide for fluid to pass there through from the inlet end 106 to the outlet end 108. For example, liquid microchannel 102 may have a circular cross-section, a flattened circular cross-section (e.g. an oval-shaped cross-section with the oval having a width greater than its height), a square-shaped cross-section, a rectangular shaped cross-section, or other appropriate shapes.

Very low pressure microchannel 104a has a first end 120a, at least one second end 122a and a conduit 124a running between the first end 120a and the at least one second end 122a. In the example microfluidic device 100 shown in the FIG. 1A, a second very low pressure microchannel 104b is also provided. Very low pressure microchannel 104b has a first end 120b, at least one second end 122b and a conduit 124b running between the first end 120b and the at least one second end 122b. Second very low pressure microchannel 104b is positioned on an opposed side of the liquid microchannel conduit 110 relative to very low pressure microchannel 104a.

A very low pressure source (not shown) is coupled to first end 120a of very low pressure microchannel 104a for applying a negative pressure to very low pressure microchannel 104a. A second very low pressure source (not shown) may also be coupled to first end 120b of very low pressure microchannel 104b for applying a negative pressure to very low pressure microchannel 104b. The negative pressure applied to the very low pressure microchannels 104a, 104b can be controlled within a range of about 0 to −90 kPa (e.g. relative to atmospheric pressure). In some embodiments, the vacuum sources (not shown) to provide the negative pressure can be a hand vacuum pump (e.g. Mityvac hand vacuum pump from Mityvac, St. Louis, Mo., USA) or any other appropriate vacuum pump such as Rotary Vane Pump and a Diaphram Pump. In some embodiments, the vacuum sources may have an integrated pressure gauge to control the negative pressure, and can be coupled to the very low pressure microchannels 104a, 104b by Tygon tubing.

Microfluidic device 100 can be formed from any material capable of containing the liquid passing through the liquid microchannel 102 (i.e. is impermeable to liquid) and providing for air to pass between the liquid microchannel conduit 110 and the very low pressure microchannel conduit 124 (i.e. is permeable to gases). For instance, microfluidic device 100 may be formed from polydimethylsiloxane ("PDMS") or tygon tubing. Accordingly, at least a portion of the liquid microchannel conduit 110 and at least a portion of the very low pressure microchannel 124 may be porous to provide for air to pass through the liquid microchannel conduit 110 and into the very low pressure microchannel 104 while inhibiting liquid from passing through the liquid microchannel conduit 110 and into the very low pressure microchannel 104. Microfluidic device 100 is also formed of a material that provides for a negative pressure applied to the very low pressure microchannel 104 to be experienced inside of the liquid microchannel 102.

Microfluidic device 100 can be formed by any appropriate technique for forming microchannels. For example, as shown in FIG. 1A, microfluidic device 100 may be formed by soft lithography techniques. For instance, microfluidic device 100 may be formed by patterning a single-layer PDMS slab (i.e. PDMS, Sylgard 184 silicone elastomer kit, Dow Corning, Midland, Mich., USA). In one specific embodiment, a mask may be designed using CAD software (i.e. AutoCAD 2010, Autodesk, Inc., Dan Rafael, Calif., USA) and formed on a silicon wafer by spin-coating an 80 μm thick SU-8 2075 film and then patterning the film using UV light through a photomask that is printed on a transparency sheet (i.e. 25 400 dpi, CAD/ART Services Inc., Bandon, Oreg., USA). The pattern formed on the wafer by photolithography is then transferred to the PDMS by molding the PDMS over the mask. Liquid inlet 130, air inlet 132, first end 120 and second ends 122 of the very low pressure microchannel 104 can be formed using a 1 mm diameter biopsy punch (e.g. Integra Miltex, Inc., Rietheim-Weilheim, Germany). The PDMS body may then then irreversibly bonded to a glass microscope slide using oxygen plasma (e.g. Harrick Plasma, Ithaca, N.Y., USA) to complete the microfluidic chip (see FIG. 1A).

In some embodiments, the liquid microchannel conduit 110 may be entirely porous to air to provide for air to pass through the liquid microchannel conduit 110 while inhibiting liquid from passing through the liquid microchannel conduit 110. Similarly, at least a portion of the very low pressure microchannel conduits 124a, 1124b may be porous to air to provide for air to pass through the very low pressure microchannel conduits 124a, 124b while inhibiting liquid from passing through the very low pressure microchannel conduits 124a, 124b (e.g. in the event that liquid passes through the liquid microchannel conduit 110). In some embodiments, the liquid microchannel conduit 110 may be entirely porous (e.g. the entire liquid microchannel conduit 110 extending from the inlet end 106 to the outlet end 108) to air to provide for air to pass through the liquid microchannel conduit 110 while inhibiting liquid from passing through the liquid microchannel conduit 110.

At first end 106 of liquid microchannel 102, there may be provided a liquid inlet 130, an air inlet 132 and an orifice 134 for forming microbubbles.

A continuous liquid phase can be inserted into the liquid microchannel 102 through the liquid inlet 130. The continuous liquid phase can be any appropriate liquid for forming microbubbles therein and for carrying microbubbles along the length of the liquid microchannel 102. For example, in some embodiments, the continuous liquid phase may be a continuous liquid phase that is commonly referenced in a medical ultrasound literature to stabilize perfluorocarbon droplets, which are vaporized in animal models for potential applications in contrast-enhanced imaging and drug delivery. For example, the continuous liquid phase may be a mixture of lipids, glycerol (e.g. from Sigma Aldrich Corporation, St. Louis, Mo., USA), and pluronic F-68 (e.g. from Fisher Scientific, Pittsburgh, Pa., USA) in a 1:1:1 volumetric ratio. In other examples, the continuous liquid phase may be prepared using 9:1 molar ratio of 1,2-distearoyl-sn-glycero-3-phosphocoline (DSPC) (e.g. from Avanti Polar Lipids, Alabaster, Ala., USA) and 1,2-distearoyl-sn-glycero-3-phosphoethanolamine-N [methoxy-(polyethylene glycol)-5000] (DSPE-PEG5000) (e.g. from Avanti Polar Lipids, Alabaster, Ala., USA) in saline (lipid concentration of 1.5 mg/mL).

In some embodiments, the continuous liquid phase includes a lipid solution, such as but not limited to lipid solutions described above, and is provided to the inlet 1130 by a constant flow rate syringe pump (e.g. Harvard Instruments, Holliston, Mass., USA). In some embodiments, the continuous liquid phase can be provided to the microfluidic device 100 at a flow rate in a range of about 1 μL to 100 μL per minute. In other embodiments, the continuous liquid phase can be provided to the microfluidic device 100 at a flow rate of about 4 μL per minute.

A dispersed gas phase is inserted into the continuous liquid phase at the inlet end 106 of the liquid microchannel 102 at the air inlet 132. Any appropriate gas phase that has components that are dissolvable in water may be used for the formation of microbubbles. In some examples, air is used as the gas phase for the formation of microbubbles. For example, pressurized air may be supplied to the air inlet 132 of the microfluidic device 100 through a control valve (not shown) using Tygon tubing (e.g. Saint gobain S.A., Courbevoie, France). In some embodiments, the control valve (e.g. Omega Engineering Inc., Norwalk, Conn., USA) may be coupled to a pressure gauge (e.g. Omega Engineering Inc., Norwalk, Conn., USA) to control the air pressure at the air inlet 132. Any appropriate pressure can be used as an inlet air pressure. In some embodiments, an inlet air pressure of 4 psi can be used in the microfluidic device 100.

In some embodiments, an interfacial tension of the mixture of the continuous liquid phase and the gas phase is 1.5 mN/m, measured using the pandent drop method.

After the liquid phase and the gas phase are provided to the liquid microchannel 102 at inlet end 106, microbubbles are formed at the inlet end 106 of the liquid microchannel 102. In some embodiments, microbubbles are formed by pinching-off microbubbles at a flow focusing orifice 134. An example of this is shown in FIG. 1B in which the flow focusing orifice 134 has a width of 20 µm. The liquid can be pumped through the microfluidic device 100 using any appropriate technique. For instance, a constant flow rate syringe pump can be used to pump the liquid through the microfluidic device. After passing through orifice 134, the microbubbles begin to flow away from the inlet end 106 of the liquid microchannel 102, through the serpentine portion of the microchannel 102, and towards the outlet end 108 of the liquid microchannel 102. In some embodiments, ~1,000 bubbles can be formed per second. In other embodiments, ~1,000,000 bubbles can be formed per second.

After formation of the microbubbles at orifice 134, the microbubbles are carried by the liquid along the liquid microchannel 102. In some embodiments, liquid microchannel 102 has a gradually decreasing channel diameter Di. For example, in the example shown in FIG. 1A, the microchannel 102 immediately downstream of the orifice 134 has a width of 200 µm, whereas as the liquid microchannel 102 extends towards the outlet end 108, the microchannel has a width of 350 µm.

Microbubbles generated at orifice 134 may shrink as they flow downstream along microchannel 102 between the inlet end 106 and the outlet end 108. In some embodiments, microbubbles generated at the orifice have diameters that are larger than the liquid microchannel 102 height. For instance, in some embodiments, the liquid microchannel 102 may have a height of about 80 µm. When the microbubbles have a diameter greater than the height of the liquid microchannel 102, the microbubbles may be confined to a discoid shape. As the microbubbles shrink as they travel towards the outlet end 108 (as described below), the diameter of the microbubbles is generally unconfined by the dimensions of the liquid microchannel 102 such that the diameter $D_f$ of the microbubbles is less than the height of the liquid microchannel 102.

Very low pressure microchannel 104a is arranged relative to liquid microchannel 102 such that at least a portion of the very low pressure microchannel conduit 124a is laterally spaced from at least a portion of the liquid microchannel conduit 110. In some embodiments, at least a portion of the very low pressure microchannel conduit 124a is laterally spaced from and parallel to at least a portion of the liquid microchannel conduit 110. For instance, as shown in FIG. 1, the curved portions of microchannel conduit 110 are laterally spaced from a portion of very low pressure microchannel conduit 124a, whereas the straight portions of microchannel conduit 110 (e.g. the portions of microchannel conduit 110 captured in FIGS. 1B-1F) are laterally spaced from and parallel to a portion of very low pressure microchannel conduit 124a.

In some embodiments, applying a negative pressure to very low pressure microchannel 104a can shrink microbubbles within the liquid microchannel 102 as the microbubbles pass along the portion of the liquid microchannel conduit 110 that is laterally spaced from, and optionally parallel to, the very low pressure microchannel conduit 124a. The negative pressure of very low pressure microchannel 104a can withdraw air from the microbubbles in the liquid microchannel 102 to shrink the microbubbles as the microbubbles travels along the portion of the liquid microchannel conduit 110 laterally spaced from, and optionally parallel to, the portion of the very low pressure microchannel conduit 124a.

In the example shown in FIG. 1A, a second very low pressure microchannel 104b is provided and arranged on an opposed side of the liquid microchannel 102 relative to very low pressure microchannel 104a. Again, as described above for very low pressure microchannel 104a, very low pressure microchannel conduit 124b is laterally spaced from at least a portion of the liquid microchannel conduit 110. In some embodiments, at least a portion of the very low pressure microchannel conduit 124b is laterally spaced from and parallel to at least a portion of the liquid microchannel conduit 110. For instance, as shown in FIG. 1, the curved portions of microchannel conduit 110 are laterally spaced from a portion of very low pressure microchannel conduit 124b, whereas the straight portions of microchannel conduit 110 (e.g. the portions of microchannel conduit 110 captured in FIGS. 1B-1F) are laterally spaced from and parallel to a portion of very low pressure microchannel conduit 124b.

In some embodiments, applying a negative pressure to very low pressure microchannel 104b can shrink microbubbles within the liquid microchannel 102 as the microbubbles pass along the portion of the liquid microchannel conduit 110 that is laterally spaced from, and optionally parallel to, the very low pressure microchannel conduit 124b. The negative pressure of very low pressure microchannel 104b can withdraw air from the microbubbles in the liquid microchannel 102 to shrink the microbubbles as the microbubbles travels along the portion of the liquid microchannel conduit 110 laterally spaced from, and optionally parallel to, the portion of the very low pressure microchannel conduit 124b.

Very low pressure microchannels 104a and 104b are spaced apart from at least a portion of liquid microchannel 102 by a spacing 150. Spacing 150 can vary along a length of liquid microchannel 102 and be configured such that a negative pressure experienced in a portion of the very low pressure microchannels 104a, 104b is also experienced in a corresponding portion of the liquid microchannel 102 that is laterally spaced from, and optionally parallel to, the portion of the very low pressure microchannels 104a, 104b. By varying spacing 150, a degree to which the negative pressure in the very low pressure microchannels 104a, 104b is experienced in the liquid microchannel 102 can be varied. In some embodiments, the spacing 150 can be in a range of about 100 µm to 200 µm. In other embodiments, spacing 150 can be about 175 µm.

In some embodiments, each very low pressure microchannel 104a, 104b can be arranged so that spacing 150 between at least a portion of the liquid microchannel 102 and corresponding laterally spaced portions of very low pressure microchannels 104a and 104b is substantially the same along a length of liquid microchannel 102. In other embodiments, each very low pressure microchannel 104a, 104b can be arranged so that spacing 150 between at least a portion of the liquid microchannel 102 and corresponding laterally spaced apart portions of very low pressure microchannels 104a and 104b vary along a length of liquid microchannel 102.

As shown in FIG. 1A, the two very low pressure microchannels 104a, 104b can be arranged relative to liquid microchannel 102 such that at least a portion of each of the very low pressure microchannel conduits 124a, 124b is laterally spaced from and parallel to a same portion of the liquid microchannel conduit 110. In other words, a portion of the liquid microchannel conduits 110 is between corresponding portions of the very low pressure microchannel conduits 124a, 124b. In these embodiments, applying a negative pressure to the very low pressure microchannels 104a, 104b (e.g. a same negative pressure in each very low pressure microchannel or a different negative pressure in each microchannel) can shrink microbubbles travelling along the liquid microchannel 102 as the microbubbles pass along the portion of the liquid microchannel conduit 110 that is laterally spaced from and parallel to each of the very low pressure microchannel conduits 124a, 124b. It should be understood that each very low pressure microchannel 104a, 104b can have a different negative pressure (e.g. between atmospheric pressure and vacuum). Again, as previously described, the negative pressure within the very low pressure microchannels 104a, 104b can withdraw air from the microbubbles in the liquid microchannel 102 to shrink the microbubbles as the microbubbles travels along the portion of the liquid microchannel conduit 110 that is laterally spaced from and parallel to the portions of the very low pressure microchannel conduits 124a, 124b.

It should be understood that more than one portion of liquid microchannel 102 can be laterally spaced from and parallel to more than one portion of very low pressure microchannels 104a, 104b. Further, it should also be understood that substantially all of liquid microchannel 102 can be laterally spaced from and parallel to a portion or several different portions of very low pressure microchannels 104a, 104b to controllably shrink microbubbles as the microbubbles travel along a path length of liquid microchannel 102.

Liquid microchannel 102 can have any shape along its length. For instance, liquid microchannel 102 can have a substantially linear shape without any curves or bends. In the example shown in FIG. 1A, liquid microchannel 102 can have a serpentine (e.g. snake-like or curved shape). Very low pressure microchannels 104a, 104b can be arranged to be continuously spaced (e.g. a length of spacing 150 is generally unchanged) along a length of the liquid microchannel 102 or can be arranged to have a variable spacing (e.g. a length of spacing 150 is variable) along a length of the liquid microchannel 102.

For instance, to achieve very low pressure microchannels 104a, 104b being continuously spaced (e.g. a length of spacing 150 is generally unchanged) along a length of the liquid microchannel 102, FIG. 1A shows liquid microchannel 102 having a serpentine (e.g. curved) shape and very low pressure microchannels 104a, 104b as interdigitated microchannels that are patterned adjacent to the serpentine liquid microchannel 102. The interdigitated very low pressure microchannels 104a, 104b are shown as each having a width 150 of about 150 µm and each being separated from the liquid microchannel 102 by a spacing 150 of about 175 µm. In the embodiment shown in FIG. 1A, all channels (e.g. liquid microchannel 102 and very low pressure microchannels 104) have a height of about 80 µm.

Two very low pressure inlets 120a, 120b are shown in FIG. 1A as being on different sides of the device 100 to provide a negative pressure to the very low pressure microchannels 104a, 104, respectively. Very low pressure inlets 120a, 120b can be positioned anywhere along the respective very low pressure microchannels 104a, 104b. For example, as shown in FIG. 1A, very low pressure inlets 120a, 120b are each positioned between inlet end 106 and outlet end 108 of the liquid microchannel 102. In this embodiment, the vacuum sources (not shown) can be configured to provide an equal negative pressure on both sides of the liquid microchannel 102 to provide for equal removal of the gas through the conduit 110 of the liquid microchannel 102. The negative pressure can be applied at any number of very low pressure microchannel inlets 124a. 124b.

Microchannel 102 generally has a consistent shape in cross-section along its length. In the example shown in FIG. 1A, microchannel 102 has a flattened circle shape, with a width W1 in a range between 10 and 1,000 microns.

Microchannel 102 can have any topographical shape along its length. For example, as shown in FIG. 1A, microchannel 102 has a serpentine shape with eight, curved 180 degree bends or turns. In this manner, microchannel 102 can be molded on a smaller footprint than a microchannel of the same length that does not have any bends or curves.

The size of the microbubbles at outlet end 108 is a function of at least the overall path length of the liquid microchannel 102 and the amount of negative pressure applied to very low pressure microchannel 104.

Figure 2:
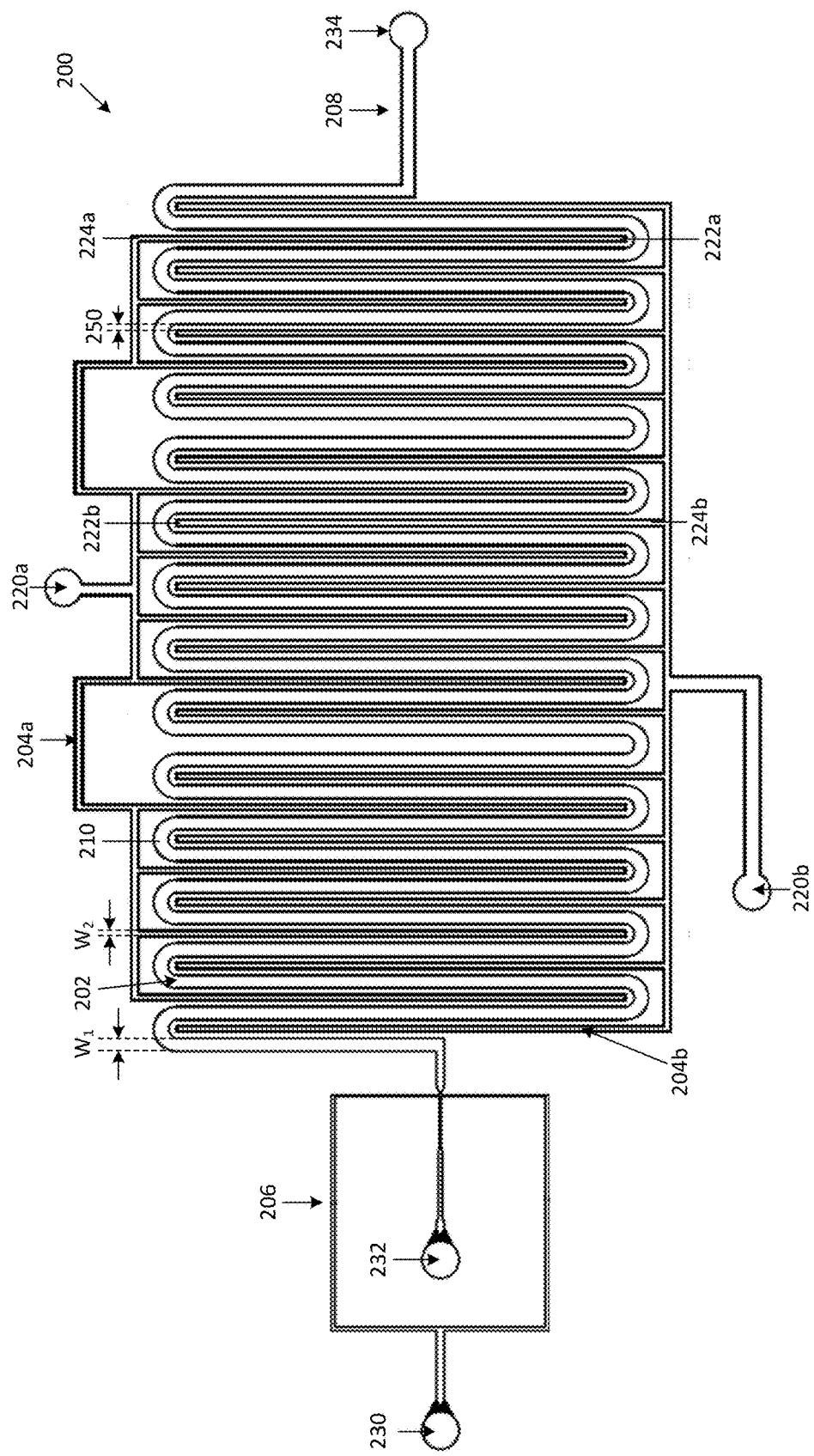
FIG. 2 is a top view of an example embodiment of a microfluidic device for microbubble generation and shrinkage, in accordance with the teachings herein.

Referring now to FIG. 2, illustrated therein is a top view of an example embodiment of a microfluidic device 200 for microbubble generation and shrinkage, in accordance with the teachings herein. It should be noted that for simplicity and clarity of illustration, reference numerals in FIG. 2 correspond to the reference numerals of FIG. 1 with increases of 100. Accordingly, in this embodiment, device 200 is shown as having a liquid microchannel 202 with a serpentine shape and two very low pressure microchannels 104a, 104b arranged to be interdigitated within 13 curves of the liquid microchannel 102.

EXAMPLES

To obtain the experimental images of the microbubbles an inverted microscope (Olympus Corp., Tokyo, Japan) and an attached high speed camera (Phantom M110, Vision Research, Wayne, N.J., USA) were used. The camera operated at 100 fps with an exposure time of 500 ms. Using ImageJ software, the initial microbubble diameter, Di, was measured immediately after they were generated at the orifice 134 (FIG. 1B). Subsequently, the final microbubble diameter, $D_f$, was measured at a fixed location in the serpentine microchannel near the outlet of the device (FIG. 1F).

To make an equivalent comparison of initial and final microbubble sizes, we convert our measurements to the initial and final volumes of the microbubbles, Vi and Vf, respectively, to determine the amount of microbubble shrinkage (details about the conversion are based on equations used in B.-U. Moon, D. K. Hwang and S. S. H. Tsai, Lab on a Chip, 2016, 8, 198-220, which is hereby incorporated by reference).

FIGS. 1B to 1F show representative experimental images of microbubbles at different locations in the liquid microfluidic channel 102 downstream of the bubble generating orifice 134. The images show that the microbubbles shrink as they flow downstream towards the outlet end 108. These images were taken when the negative pressure applied to very low pressure microchannels 104a, 104b was about −50 kPa.

The size of these microbubbles are known to depend on the size of the orifice 134, inlet air pressure, liquid-air surface tension, and the continuous liquid flowrate. In the experiments, the orifice size, inlet air pressure, liquid-air surface tension, and continuous liquid flow rate are all held constant. Therefore, the initial microbubble volume, Vi=1.5 nL, that was measured immediately downstream of the orifice, was approximately the same in all of the experiments.

Figure 3:
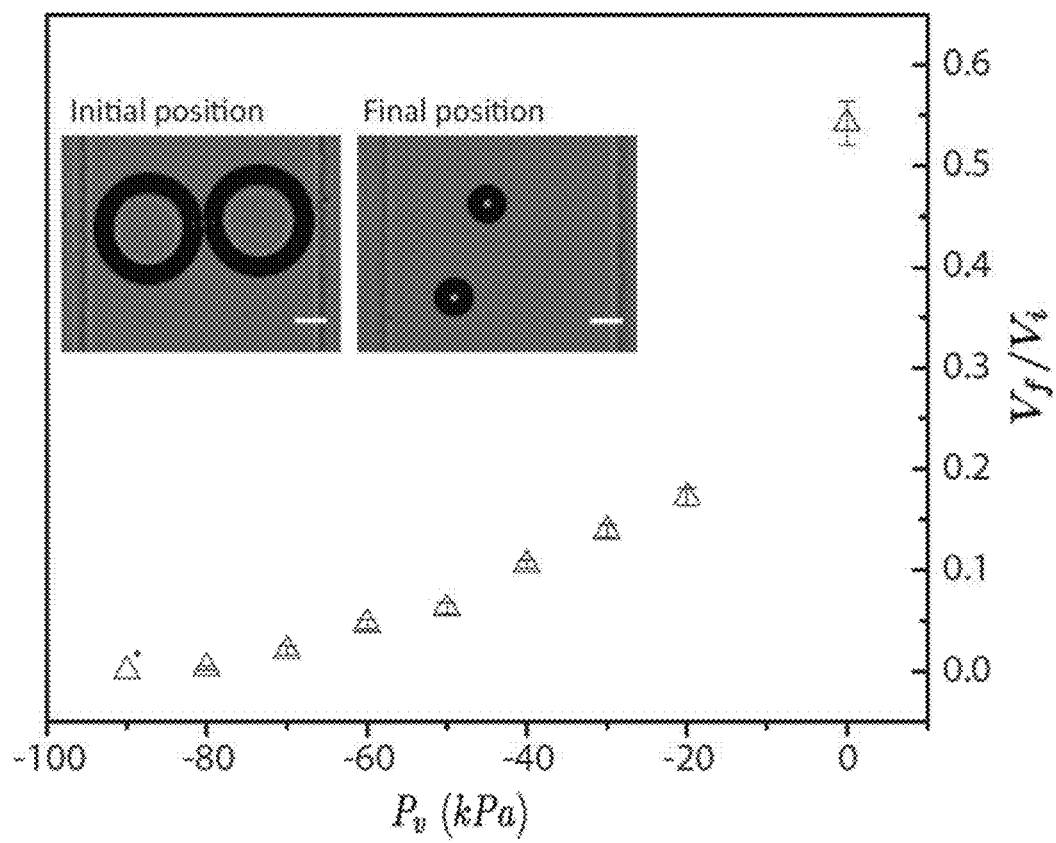
FIG. 3 is a graph showing normalized final microbubble volume ($V_f=V_i$) versus an applied channel pressure in very low pressure microchannels for the microfluidic device of FIG. 1A.

FIG. 3 shows a plot of a normalized final microbubble volume, Vf/Vi, versus the applied vacuum pressure, Pv, in the very low pressure microchannels 104a, 104b. Here, the final microbubble volume, Vf, which is measured at a fixed location near the outlet 108 of the liquid microchannel 102 is normalized by the initial volume, Vi, which is measured immediately downstream of the bubble generating orifice 134. The inset of FIG. 3 shows two representative images of the microbubbles at the initial and final measurement locations, corresponding to initial and final volumes Vi and Vf, respectively.

When the applied vacuum pressure, Pv=0, the final microbubble volume Vf is approximately 55% of the initial microbubble volume, Vi. This microbubble shrinking effect, in the absence of an applied vacuum pressure, may be due to the high pressure of the gas and liquid in the liquid microchannel 102, which is a result of the pressure-driven nature of the flows. The pressure in the microchannel 102 is higher than atmospheric pressure, so according to Henry's law, the molecular components of air in the microbubbles will become more soluble in the continuous liquid. Convective liquid-gas mass transfer due to the moving microbubbles may also contribute to microbubbles shrinking along the serpentine microchannel. However, the passive dissolution of gas into the continuous liquid phase is a slow process, so relying on this passive mechanism alone is not sufficient to rapidly generate microbubbles that are important for biomedical ultrasound and therapeutics applications.

The results in FIG. 3 also show that there is a drastic and monotonic decrease in final microbubble volumes, Vf=Vi, with increasing magnitude of the applied vacuum pressure, Pv. This evidence suggests that the applied vacuum pressure Pv, which is controllable, is a good control parameter for the resulting microbubble size. Importantly, the microbubbles can be shrunk to diameters (Df=1-7 $\mu$m) that are desirable to biomedical ultrasound and therapeutics applications. Namely, an applied vacuum pressure Pv=−60 kPa resulted in final microbubble volumes Vf=74 pL, which is equivalent to a microbubble diameter Df=52 $\mu$m.

PDMS is permeable to various components of air, namely gaseous oxygen, nitrogen, and carbon dioxide. As described herein, in accordance with the teachings herein, a negative pressure (i.e. a pressure that is lower than atmospheric pressure) environment was created in the very low pressure microchannels 104a, 104b adjacent to the liquid microchannel 102. The continuous liquid phase may not be degassed. The liquid is generally initially saturated with dissolved components of air at atmospheric pressure. In the microfluidic device 100, the negative pressure in the very low pressure microchannels 104 may cause gaseous components of air that are originally dissolved in the liquid continuous phase in the liquid microchannel 102 to permeate through the PDMS wall and exit via very low pressure microchannels 104a, 104b. Concurrently, the air inside the microbubbles may dissolve into the surrounding continuous phase as the microfluidic device 100 attempts to continuously attain thermodynamic equilibrium, causing the microbubbles to shrink.

The resulting microbubbles after shrinkage are stable because the shrinking process removes molecules of air from the microbubbles, instead of, for example, compressing the microbubbles in a high pressure environment. Therefore, the microbubbles remain in a thermodynamic equilibrium state in the continuous liquid phase even after returning to an atmospheric pressure environment.

Figure 4A:
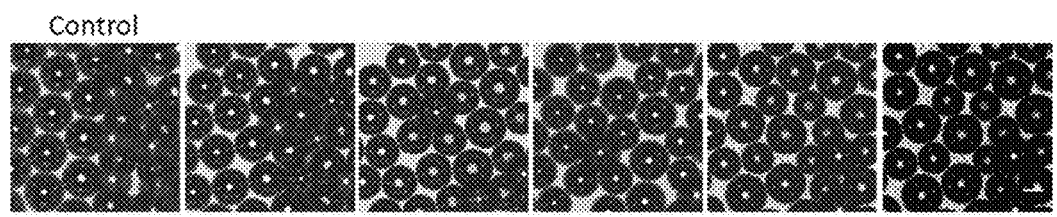
FIG. 4A shows representative sequential images of microbubbles collected at the outlet of the microfluidic device of FIG. 1A when the applied channel pressure to the very low pressure microchannels, $P_v=0$ kPa.
Figure 4B:
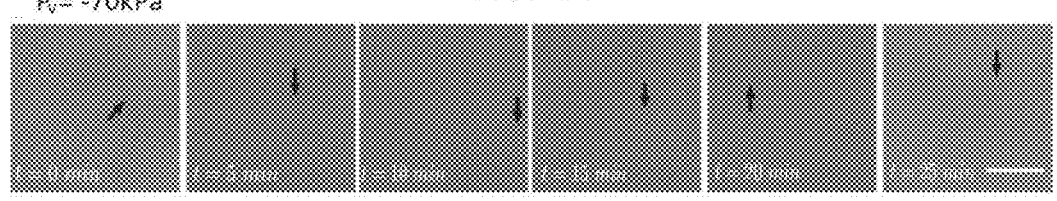
FIG. 4B shows representative sequential images of microbubbles collected at the outlet of the microfluidic device of FIG. 1A when the applied channel pressure to the very low pressure microchannels, $P_v=-70$ kPa, where the arrows indicate the location of the microbubbles in the sample.

FIGS. 4A and 4B show representative experimental images of the microbubbles collected at the outlet 108 of the microfluidic device 100 observed using 10× and 50× microscope objectives, respectively at different points in time. In FIG. 4A, the microbubbles are from a control experiment where the vacuum pressure, Pv=0 kPa. FIG. 4B shows microbubbles from an experiment where the vacuum pressure, Pv=−70 kPa. An initial time t=0 min is defined as the moment when the sample was liquid collected from the outlet 108. Subsequent sequential images are taken at intervals of 5 min apart. For this particular experiment, the vacuum pressure Pv=−70 kPa, which resulted in microbubbles collected that have diameters, Df, in the range of 1-7 $\mu$m, the desired size for ultrasound contrast agents. Both sets of images in FIG. 4 show that the collected microbubbles approximately maintain their size-stability even after 25 min.

Figure 5:
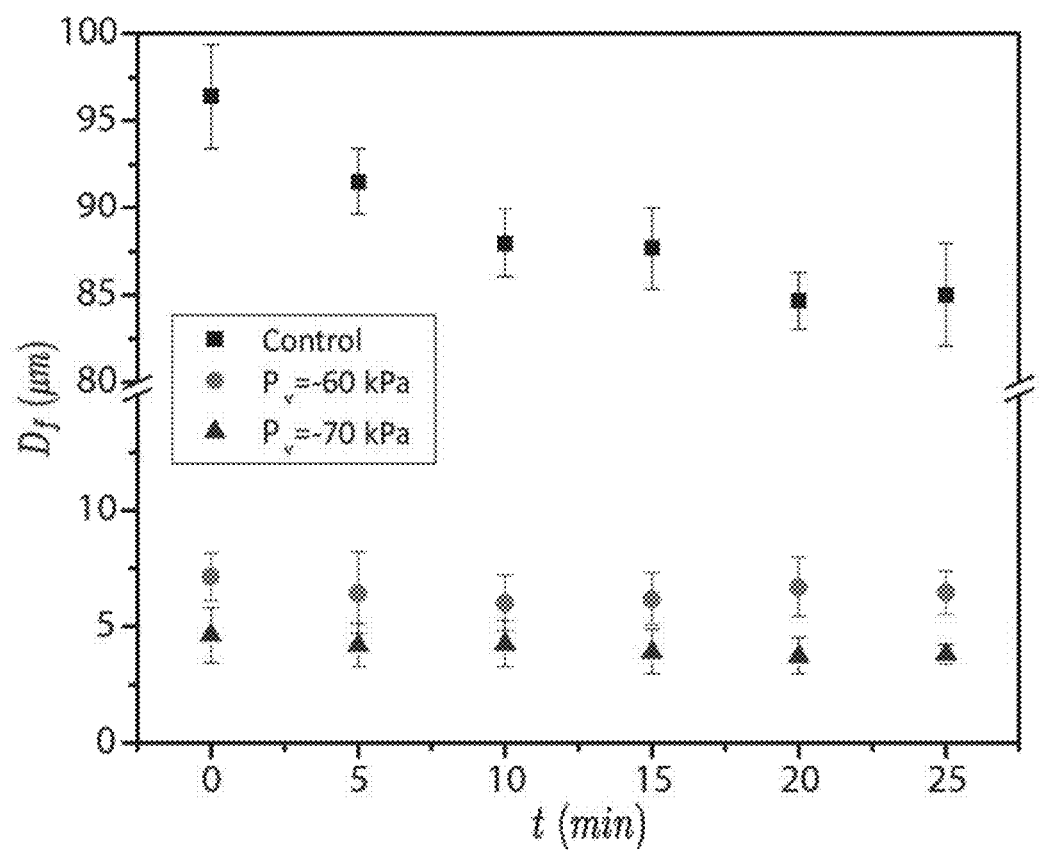
FIG. 5 is a graph of a diameter $D_f$ of collected microbubbles versus time t for the microfluidic device of FIG. 1.

FIG. 5 is a plot of the diameter, Df, of collected microbubbles, versus time t. Here, the applied vacuum pressure Pv was 0, −60, and −70 kPa. The plot shows that the diameter $D_f$ of the microbubbles decreases by approximately 10% over 25 minutes for the control experiment, and remains very stable for the experiments where the applied vacuum pressure Pv=−60 and −70 kPa. Critically, this result is evidence that the microfluidic approach for generating and vacuum shrinking microbubbles is capable of making microbubbles that are in the relevant length scale of 1-7 $\mu$m diameter.

The invention claimed is:

1. A method of controlling a size of a microbubble, the method comprising:
    forming a microbubble in a liquid at an inlet end of a liquid microchannel, the liquid microchannel having an outlet end spaced from the inlet end and a liquid microchannel conduit extending between the inlet end and the outlet end;
    propelling the liquid along a length of the liquid microchannel from the inlet end towards the outlet end, the liquid carrying the microbubble from the inlet end towards the outlet end; and
    applying a negative pressure to a first very low pressure microchannel, the first very low pressure microchannel having a first end, a second end spaced from the first end and a first very low pressure microchannel conduit extending between the first end and the second end and having a portion thereof being laterally spaced from and adjacent to a portion of the liquid microchannel conduit, the negative pressure withdrawing air from the microbubble in the liquid microchannel to shrink the microbubble as the microbubble travels along the portion of the liquid microchannel conduit laterally spaced from and adjacent to the portion of the first very low pressure microchannel conduit.

2. The method of claim 1, wherein the method further comprises applying the negative pressure to the first very low pressure microchannel and to a second very low pressure microchannel, the second very low pressure microchannel having a first end, a second end spaced from the first end and a second very low pressure microchannel conduit extending between the first end and the second end, a portion of the second very low pressure microchannel conduit being laterally spaced from and adjacent to an opposed side of the portion of the liquid microchannel conduit relative to the portion of the first very low pressure microchannel conduit.

3. The method of claim 1, wherein the portion of the first very low pressure microchannel conduit laterally spaced from and adjacent to the portion of the liquid microchannel conduit is parallel to the portion of the liquid microchannel conduit.

4. The method of claim 2, wherein the portions of the first very low pressure microchannel conduit and the second very low pressure microchannel conduit that are laterally spaced from and adjacent to the portion of the liquid microchannel conduit are both parallel to the portion of the liquid microchannel conduit.

5. The method of claim 1, wherein after the forming of the microbubble, the microbubble has a width in a range of about 10 to 1000 μm and after the shrinking of the microbubble the microbubble has a width in a range of about 1 to 7 μm.

6. The method of claim 1, wherein the negative pressure is in a range of about 0 to 90 kPa below atmospheric pressure.

7. The method of claim 1, wherein the negative pressure is in a range of about 50 to 70 kPa below atmospheric pressure.

8. The method of claim 1, wherein the liquid is introduced into the microchannel at a flow rate in a range of about 1 μL per minute to about 100 μL per minute.

9. The method of claim 1, wherein the liquid is introduced into the microchannel at a flow rate of about 4 μL per minute.

10. An apparatus for shrinking microbubbles, the apparatus comprising:
a liquid microchannel having an inlet end, an outlet end spaced from the inlet end and a liquid conduit extending between the inlet end and the outlet end, the liquid microchannel housing a liquid having a microbubble dispersed in the liquid, the microbubble travelling along with the liquid in the liquid microchannel from the inlet end to the outlet end; and
a first very low pressure microchannel having a first end, a second end spaced from the first end and a first very low pressure microchannel conduit extending between the first end and the second end, the first end of the first very low pressure microchannel being coupled to a vacuum source configured for creating a negative pressure in the first very low pressure microchannel;
wherein a portion of the first very low pressure microchannel conduit is laterally spaced from and adjacent to a portion of the liquid microchannel conduit and the negative pressure is configured to withdraw air from the microbubble in the liquid microchannel conduit in order to shrink the microbubble as the microbubble travels along the portion of the liquid microchannel conduit laterally spaced from and adjacent to the portion of the first very low pressure microchannel conduit.

11. The apparatus of claim 10, further comprising a second very low pressure microchannel, the second very low pressure microchannel having a first end, a second end spaced from the first end and a second very low pressure microchannel conduit extending between the first end and the second end, the first end of the second very low pressure microchannel being coupled to a vacuum source for creating a negative pressure in the second very low pressure microchannel, a portion of the second very low pressure microchannel conduit being laterally spaced from and adjacent to an opposed side of the portion of the liquid microchannel conduit relative to the portion of the first very low pressure microchannel conduit.

12. The apparatus of claim 10, wherein the portion of the first very low pressure microchannel conduit laterally spaced from and adjacent to the portion of the liquid microchannel conduit is parallel to the portion of the liquid microchannel conduit.

13. The apparatus of claim 11, wherein the portions of the first and second very low pressure microchannel conduits laterally spaced from and adjacent to the portion of the liquid microchannel conduit are both parallel to the portion of the liquid microchannel conduit.

14. The apparatus of claim 10, wherein a spacing between the portion of the liquid microchannel conduit and the portion of the first very low pressure microchannel conduit is about 175 μm.

15. The apparatus of claim 10, wherein the liquid microchannel has a liquid microchannel width and the liquid microchannel width decreases along a length of the liquid microchannel between the inlet end and the outlet end.

16. The apparatus of claim 10, wherein the first very low pressure microchannel has a first very low pressure microchannel width of about 150 μm.

17. The apparatus of claim 10, wherein the negative pressure is in a range of about 0 to 90 kPa below atmospheric pressure.

18. The apparatus of claim 10, wherein the negative pressure is in a range of about 50 to 70 kPa below atmospheric pressure.

19. The apparatus of claim 10, wherein the liquid is introduced into the liquid microchannel at a flow rate of about 4 μL per minute.

20. The apparatus of claim 10, wherein the liquid microchannel has a serpentine shape and the first very low pressure microchannel is arranged to be interdigitated within curves of the liquid microchannel.

* * * * *